(12) United States Patent
Su et al.

(10) Patent No.: US 9,700,832 B2
(45) Date of Patent: Jul. 11, 2017

(54) STERICALLY HINDERED AMINES AND ASSOCIATED METHODS

(71) Applicant: Huntsman Petrochemical LLC, The Woodlands, TX (US)

(72) Inventors: Wei-Yang Su, Spring, TX (US); Robert A. Grigsby, Jr., Spring, TX (US); Jingjun Zhou, The Woodlands, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

(21) Appl. No.: 15/070,050

(22) Filed: Mar. 15, 2016

(65) Prior Publication Data

US 2016/0193562 A1 Jul. 7, 2016

Related U.S. Application Data

(63) Continuation of application No. 13/989,137, filed as application No. PCT/US2011/061604 on Nov. 21, 2011, now Pat. No. 9,352,271.

(60) Provisional application No. 61/418,425, filed on Dec. 1, 2010.

(51) Int. Cl.
| | |
|---|---|
| *B01D 53/48* | (2006.01) |
| *B01D 53/14* | (2006.01) |
| *C07C 217/50* | (2006.01) |
| *C09K 3/00* | (2006.01) |

(52) U.S. Cl.
CPC ..... *B01D 53/1462* (2013.01); *B01D 53/1468* (2013.01); *B01D 53/1493* (2013.01); *C07C 217/50* (2013.01); *C09K 3/00* (2013.01); *B01D 2252/2041* (2013.01); *B01D 2252/20405* (2013.01); *B01D 2252/20426* (2013.01); *B01D 2252/20484* (2013.01); *B01D 2252/504* (2013.01); *B01D 2256/16* (2013.01); *B01D 2256/20* (2013.01); *B01D 2256/24* (2013.01); *B01D 2257/304* (2013.01); *B01D 2257/504* (2013.01); *B01D 2258/0283* (2013.01); *Y02P 20/152* (2015.11)

(58) Field of Classification Search
None
See application file for complete search history.

(56) References Cited

U.S. PATENT DOCUMENTS

| | | | |
|---|---|---|---|
| 4,405,811 | A | 9/1983 | Stogryn et al. |
| 4,471,138 | A | 9/1984 | Stogryn |
| 4,618,481 | A | 10/1986 | Heinzelmann et al. |
| 4,665,195 | A | 5/1987 | Stogryn et al. |
| 4,894,178 | A | 1/1990 | Ho et al. |
| 7,196,033 | B2 | 3/2007 | Renken et al. |
| 7,683,007 | B2 | 3/2010 | Renken et al. |
| 2006/0069237 | A1 | 3/2006 | Bentley et al. |
| 2010/0037775 | A1 | 2/2010 | Siskin et al. |

FOREIGN PATENT DOCUMENTS

EP 0087856 A 9/1983

*Primary Examiner* — Anita Nassiri Motlagh
(74) *Attorney, Agent, or Firm* — Huntsman International LLC

(57) ABSTRACT

Amine compositions comprising sterically hindered amines and associated methods are provided. In some embodiments, amine compositions of the present disclosure may be useful for selective removal of $H_2S$ from an acidic gas stream.

7 Claims, 1 Drawing Sheet

STERICALLY HINDERED AMINES AND ASSOCIATED METHODS

CROSS-REFERENCE TO RELATED APPLICATIONS

This application claims the benefit of U.S. patent application Ser. No. 13/989,137, filed Jul. 10, 2013, currently pending, and U.S. Provisional Patent Application Ser. No. 61/418,425 filed Dec. 1, 2010, the entire disclosures of which are incorporated herein by reference.

FIELD OF THE INVENTION

The present disclosure generally relates to sterically hindered amines, and more specifically, to the production of sterically hindered amines from polyethylene glycol and tertiarybutylamine and their use in acidic gas removal.

BACKGROUND

Various amine solutions have been used for the removal of acidic gases from gases and liquids. Common acidic gases may include, $CO_2$, $H_2S$, $CS_2$, HCN, COS and oxygen and sulfur derivatives of $C_1$ to $C_4$ hydrocarbons. In general, the treatment of gases and liquids containing acidic gases, such as $CO_2$ and $H_2S$, with certain amine solutions typically results in the simultaneous removal of substantial amounts of both $CO_2$ and $H_2S$. However, in some instances, it may be desirable to treat acidic gas mixtures containing both $CO_2$ and $H_2S$ so as to selectively remove $H_2S$ from the mixture, thereby minimizing removal of the $CO_2$. Selective removal of $H_2S$ results in a relatively high $H_2S/CO_2$ ratio in the separated acid gas which may aid in the conversion of $H_2S$ to elemental sulfur using the Claus process.

Sterically hindered amines have been used for the selective removal of $H_2S$ from gaseous mixtures. One method of producing sterically hindered amines has included the catalytic tertiarybutylamination of triethylene glycol to produce bis-(tertiarybutylaminoethoxy) amine and ethoxyethanoltertiarybutylamine. However, this process has drawbacks because under $CO_2$ rich conditions and/or high bis-(tertiarybutylaminoethoxy) ethane content, the amine salt can precipitate out of solution during the acid gas removal process and fouling of the equipment may occur. In addition, the costs associated with the starting reaction materials necessary to produce sterically hindered amines are generally high and prior art processes have generally yielded high levels of undesirable by-products, resulting in only 25-30% useable product.

SUMMARY

The present disclosure generally relates to sterically hindered amines, and more specifically, to the production of sterically hindered amines from polyethylene glycol and tertiarybutylamine and their use in acidic gas removal.

In one embodiment, the present disclosure provides an amine composition comprising a mixture of at least two sterically hindered amines comprising a first amine with the formula:

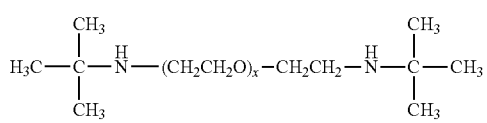

and a second amine with the formula:

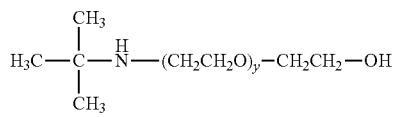

wherein x is an integer from 3 to 14; y is an integer from 3 to 14, and the weight ratio of the first amine to the second amine is about 2.5:1 to about 6:1.

In another embodiment, the present disclosure provides a method of making an amine composition comprising reacting a polyethylene glycol with a tertiarybutylamine in the presence of a nickel-based hydrogenation catalyst to form an amine composition comprising a mixture of at least two sterically hindered amines, wherein the amine composition comprises at least a first amine with the formula:

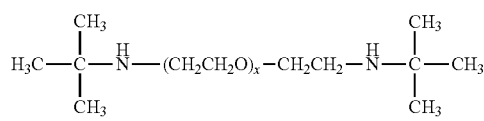

and a second amine with the formula:

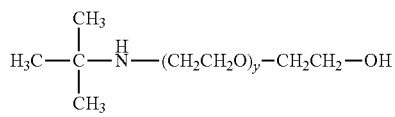

wherein x is an integer from 3 to 14; y is an integer from 3 to 14, and the weight ratio of the first amine to the second amine is about 2.5:1 to about 6:1.

In yet another embodiment, the present disclosure provides a method comprising contacting a gaseous stream comprising sulfur-containing compounds with an amine composition comprising a mixture of at least two sterically hindered amines, wherein the amine composition comprises at least a first amine with the formula:

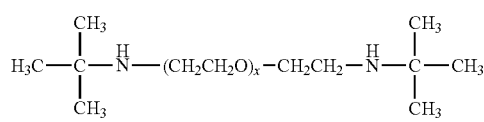

and a second amine with the formula:

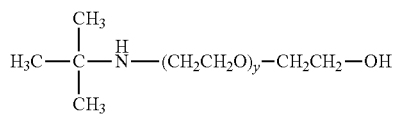

wherein x is an integer from 3 to 14; y is an integer from 3 to 14, and the weight ratio of the first amine to the second amine is about 2.5:1 to about 6:1.

The features and advantages of the present invention will be readily apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 1:
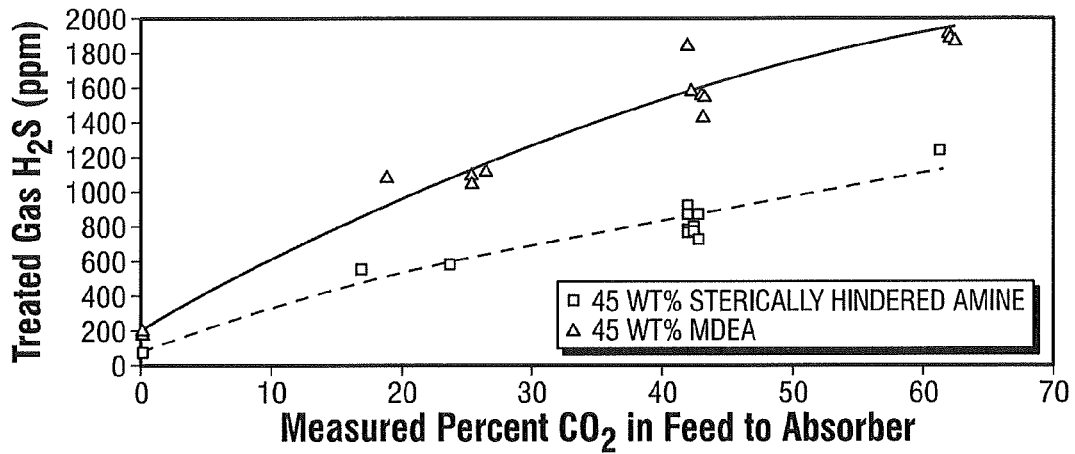
FIG. 1 is a graph showing the effect of $CO_2$ concentration on $H_2S$ removal.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to sterically hindered amines, and more specifically, to the production of sterically hindered amines from polyethylene glycol and tertiarybutylamine and their use in acidic gas removal.

The present disclosure is based, at least in part, on the observation that under certain conditions, such as $CO_2$ rich conditions and/or high bis-(tertiarybutylaminoethoxy) ethane content, certain amines for selectively removing $H_2S$ gas may become phase separated. In some embodiments, the present disclosure addresses this problem by, among other things, reacting a higher molecular weight polyethylene glycol with a tertiarybutylamine to produce a mixture of sterically hindered amines that provides good performance without the problem of phase separation. In addition, in some embodiments, the sterically hindered amines of the present disclosure may be made without the need for a solvent, thereby simplifying their production. Furthermore, in some embodiments, the methods of the present disclosure may be considered more "environmentally friendly" in that they produce higher yields of desirable amine products with minimal to no production of undesirable by-products, which may also reduce the costs associated with making sterically hindered amines.

In one embodiment, the present disclosure provides an amine composition comprising a mixture of at least two sterically hindered amines with the following formulas:

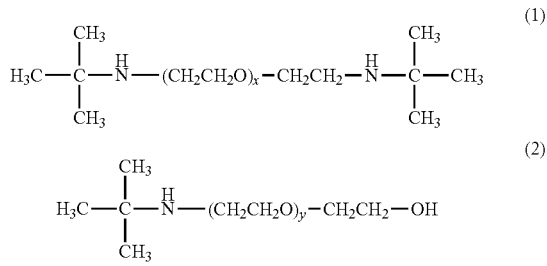

wherein x is an integer ranging from 3 to 14, y is an integer ranging from 3 to 14, and the weight ratio of a first sterically hindered amine (1) to a second sterically hindered amine (2) is about 2.5:1 to about 6:1. In some embodiments, the weight ratio of a first sterically hindered amine (1) to a second sterically hindered amine (2) is about 4:1.

In other embodiments, an amine composition of the present disclosure may comprise a mixture of at least two sterically hindered amines, a first sterically hindered amine having the chemical formula shown in (1) wherein x is an integer ranging from 7 to 14; and a second sterically hindered amine having the chemical formula shown in (2) wherein y is an integer ranging from 7 to 14.

In addition to the above mentioned amine compositions, the present disclosure also provides methods of making these amine compositions comprising reacting a polyethylene glycol with a tertiarybutylamine in the presence of a nickel-based hydrogenation catalyst. The polyethylene glycol suitable for use in the present disclosure generally has a molecular weight between about 180 to about 1000 grams per mole (g/mol). In some specific embodiments, the polyethylene glycol may have a molecular weight between about 180 to about 400 g/mol. In some specific embodiments, the polyethylene glycol may have a molecular weight between about 200 to about 300 g/mol.

Nickel-based hydrogenation catalysts suitable for use in the present disclosure may include any nickel based catalyst capable of catalyzing a reaction between polyethylene glycol and a tertiarybutyl amine. In one embodiment, a suitable hydrogenation catalyst comprises those nickel-based catalysts disclosed in U.S. Pat. Nos. 7,683,007 and 7,196,033, both of which are hereby incorporated by reference in their entirety. As will be recognized by one of skill in the art, the hydrogenation catalyst may be in any suitable form, including but not limited to, pellets, tablets, extrudates, spheres, etc. Additionally, a suitable catalyst can either be unsupported or deposited on a support material, as is known to those skilled in the art, such as alumina, silica, etc.

In some embodiments, reduction of the hydrogenation catalyst may be carried out in situ while conducting the process by the presence of hydrogen. Hydrogen, however, is not essential to conducting the process but may be employed, for example, to minimize catalyst deactivation.

In some embodiments, the sterically hindered amines of the present disclosure may be made without the need for a solvent, thereby simplifying their production. However, in some embodiments, an inert solvent may be included in the reaction medium if desired. Examples of suitable solvents may include, but are not limited to, a cyclic or linear ether or a hydrocarbon containing compound in which the reactants will dissolve.

The amination process may be carried out in any suitable reactor, including, but not limited to, a fixed-bed reactor, a fluid-bed reactor, a continuous stirred reactor, or a batch reactor. In one embodiment, the reaction of polyethylene glycol with a tertiarybutylamine may be carried out in a reactor under a pressure of about 500 to about 3000 psig and a temperature of from about 160° C. to about 240° C.

In some embodiments, the sterically hindered amines of the present disclosure may be placed in a liquid medium prior to use, such as water, an organic solvent and mixtures thereof. In addition, the sterically hindered amines may also be used in conjunction with a wide range of additives typically employed in selective gas removal processes, such as anti-foaming agents, antioxidants, corrosion inhibitors, etc. in an effective amount. In some embodiments, the sterically hindered amines of the present disclosure may also be used in conjunction with a strong acid, such as sulfuric acid, sulfurous acid, phosphoric acid, phosphorous acid, pyrophosphoric acid, acetic acid, formic acid, adipic acid, benzoic acid, etc.

As mentioned above, the sterically hindered amines of the present disclosure may be useful in selectively removing $H_2S$ from an acidic gas mixture. Acidic gas mixtures suitable for use in the present disclosure include any gas mixture that comprises an acidic gas for which acid gas removal is desired. Examples of suitable acidic gas mixtures are those comprising $H_2S$, and optionally other gases such as $CO_2$, $N_2$, $CH_4$, $H_2$, CO, COS, HCN, $C_2H_4$, $NH_3$, etc. Acidic gas mixtures may include various types of gases, including, but not limited to, combustion gases, refinery gases, town gas, natural gas, syn gas, water gas, propane, propylene, heavy hydrocarbon gases, etc.

In one embodiment, the present disclosure also provides a method for removing sulfur-containing compounds from a gaseous stream comprising contacting the gaseous stream with an amine composition of the present disclosure. In general, the gaseous stream and an amine composition of the present disclosure may be brought into contact using any conventional means, such as a tower or packed vessel. For example, in one embodiment, a gaseous stream may be fed into a lower portion of an absorption tower while an amine composition of the present disclosure is fed into an upper portion of the tower. The gaseous stream and the amine composition may come into contact with each other such that sulfur-containing compounds, such as $H_2S$, may be selectively absorbed by the amine composition. The amine composition containing the selectively absorbed sulfur-containing compounds may then emerge near the bottom or lower portion of the tower, which the remaining normally gaseous stream, emerges from the upper portion of the tower.

In some embodiments, after contacting the gaseous stream with an amine composition of the present disclosure, the amine composition containing the sulfur-containing compounds may be at least partially regenerated so that it may be reused.

To facilitate a better understanding of the present invention, the following examples of certain aspects of some embodiments are given. In no way should the following examples be read to limit, or define, the entire scope of the invention.

EXAMPLES

Example 1: Preparation of PEG-240

About 16 pounds of diethylene glycol and 130 grams of dimethylcyclohexylamine were charged to an 8-gallon reactor. The reactor was then purged with nitrogen and heated to about 85° C. Then, about 20 pounds of ethylene oxide were added to the reactor, as the temperature of the reactor was maintained at around 90° C. Upon the conclusion of the reaction, the reaction mixture was purged with nitrogen at about 80° C. for about 20 minute and then screen filtered. The resulting product was analyzed to have a hydroxyl value of 469.7 mg KOH/g.

Example 2: Preparation of Amine

PEG-240 from Example 1 and tertiarybutylamine were each continuously fed to a tubular reactor that was charged with 250 cc of a nickel catalyst at feed rates of 120 g/hr and 300 g/hr, respectively. The reactor pressure and temperature (hot oil temperature) were maintained at 2000 psig and 200° C. The reactor effluent was stripped of excess tertiarybutylamine and other light materials. The resulting product was analyzed to contain 4.28 meq/g of total amine.

Example 3: Preparation of Amine from TEG

Triethylene glycol and tertiarybutylamine were each continuously fed to a tubular reactor that was charged with 250 cc of a nickel catalyst at feed rates of 115 g/hr and 300 g/hr, respectively. The reactor pressure and temperature (hot oil temperature) were maintained at 2000 psig and 200° C. The reactor effluent was stripped of excess tertiarybutylamine and other light materials. The resulting product was analyzed to contain 5.72 meq/g of total amine.

Figure 2:
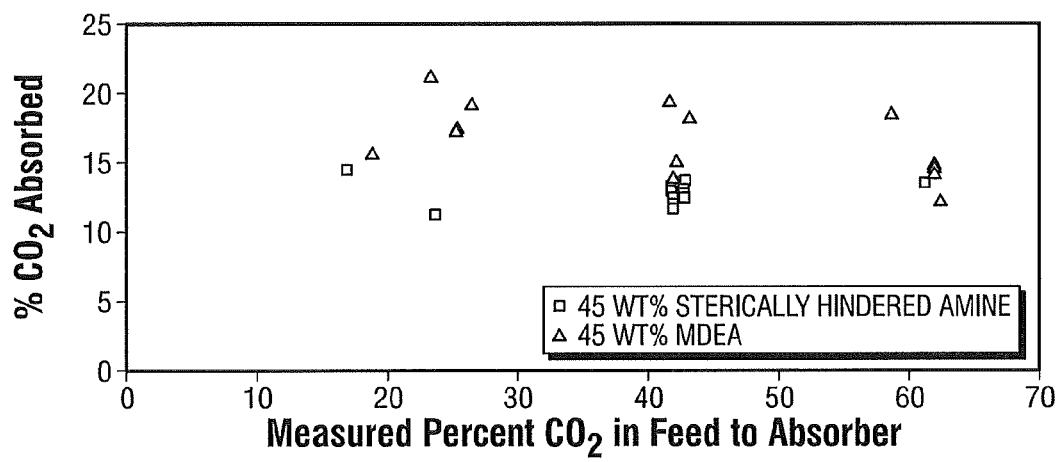
FIG. 2 is a graph showing the effect of $CO_2$ concentration effect on $CO_2$ absorption.

Example 4: Effect of $CO_2$ Concentration on $H_2S$ Removal and $CO_2$ Absorption 13500 grams of a 45 wt % sterically hindered amine solution were prepared and charged to a gas treating unit containing an absorber and a stripper connected together in a continuous flow. The lean amine temperature was controlled at approximately 70° C., while the stripper was heated to approximately 117° C. The $H_2S$, $CO_2$ and $N_2$ flowrate into the absorber was varied to obtain the desired $CO_2$ concentration (0 to 65%) and $H_2S$ concentration (6000 ppm). The amine circulation flow was controlled at 115 ml/min. After approximately 4 hours, the gas treating unit had equilibrated and samples of the gas coming off the absorber and stripper were collected and analyzed by on line gas chromatograph. The volume of gas coming in and out of the absorber was also measured. The same procedures were repeated for 45% MDEA. The results are shown in FIG. 1 and FIG. 2. The data show the sterically hindered amine has much better scrubbing of $H_2S$ compared to MDEA and have similar performance in terms of $CO_2$ absorption. Accordingly, an amine composition of the present disclosure demonstrates a higher selectivity for $H_2S$ compared to MDEA.

Figure 3:
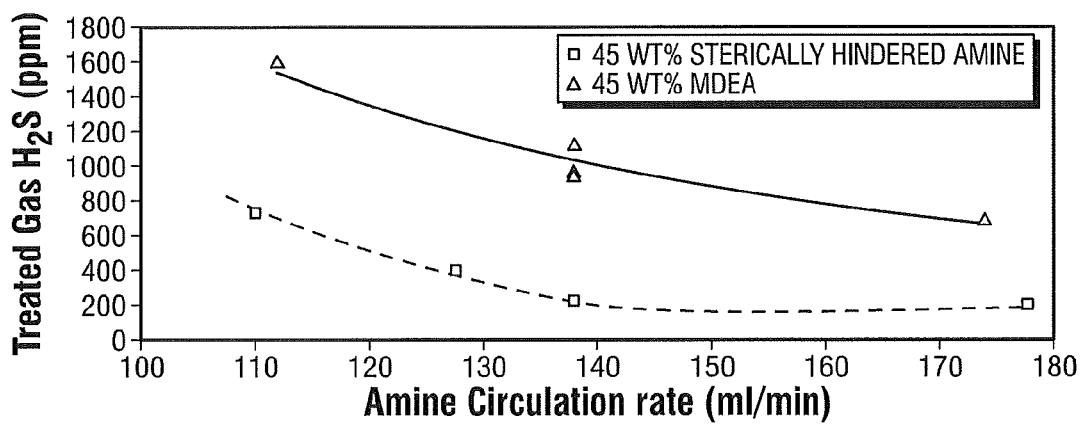
FIG. 3 is a graph showing the change of $H_2S$ in a treated gas as a function of the amine circulation rate.

Example 5: Effect of Amine Circulation Flow on $H_2S$ Removal 13500 grams of a 45 wt % sterically hindered amine solution were prepared and charged to a gas treating unit containing an absorber and a stripper connected together in a continuous flow. The lean amine temperature was controlled at approximately 70° C. while the stripper was heated to approximately 117° C. The $H_2S$, $CO_2$ and $N_2$ flowrate into the absorber were controlled at the desired rate to obtain the approximate 43% $CO_2$ and 6000 ppm $H_2S$ in the feed. The amine circulation flow was varied from 110 ml/min to 180 ml/min. After approximately 4 hours, the gas treating unit had equilibrated and samples of the gas coming off the absorber and stripper were collected and analyzed by on line gas chromatograph. The volume of gas coming in and out of the absorber was also measured. The same procedures were repeated for 45% MDEA. The results are shown in FIG. 3. The data show the sterically hindered amine has much better scrubbing of $H_2S$ compared to MDEA.

Example 6: Effect of Adding Phosphoric Acid on $H_2S$ Removal 13500 grams of a 45 wt % sterically hindered amine solution were prepared and charged to a gas treating unit containing an absorber and a stripper connected together in a continuous flow. The lean amine temperature was controlled at approximately 70° C. while the stripper was heated to approximately 117° C. $H_2S$, $CO_2$ and $N_2$ flowrate into the absorber were controlled at the desired rate to obtain the approximate 43% $CO_2$ and 6000 ppm $H_2S$ in the feed. The amine circulation flow was controlled at 200 ml/min. After approximately 4 hours, the gas treating unit had equilibrated and samples of the gas coming off the absorber and stripper were collected and analyzed by on line gas chromatograph. 34 grams of a 85% phosphoric acid solution was then injected into the stripper reboiler with $N_2$. The samples from the absorber and stripper were collected periodically until the treated gas reading was steady and the data were recorded. The lean and rich samples were also collected and $H_2S$ content was determined by titration with silver nitrate. The same procedures (with and without phosphoric acid added) were repeated for 45% MDEA. The results are shown in Table 1 below. The data demonstrate a sterically hindered amine with a small amount of phosphoric acid addition significantly reduces the $H_2S$ in the treated gas. The acid addition didn't improve the $H_2S$ treating capability of 45% MDEA due to the already lower lean loading in the MDEA (3 grain/gallon before acid addition) and further reducing the lean loading didn't improve the performance.

TABLE 1

Treated $H_2S$ (ppm) from absorber (200 ml/min amine circulation rate)

| | No acid added in the solution | 34 grams of Phosphoric acid in the solution |
|---|---|---|
| 45% MDEA solution | 501 | 500 |
| 45% Sterically hindered amine solution | 292 | 205 |

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
contacting a gaseous stream comprising sulfur-containing compounds with an amine composition comprising a mixture of at least two sterically hindered amines obtained from the reaction of a polyethylene glycol with a tertiarybutylamine in the presence of a nickel-based hydrogenation catalyst wherein the at least two sterically hindered amines comprise a first amine with the formula:

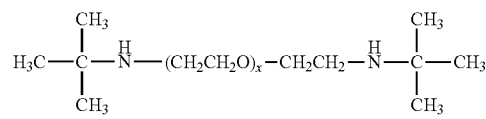

and a second amine with the formula:

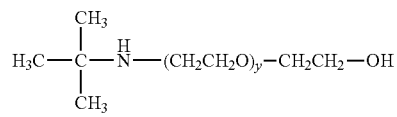

wherein x is an integer from 3 to 14; y is an integer from 3 to 14, and the weight ratio of the first amine to the second amine is about 2.5:1 to about 6:1.

2. The method of claim 1 further comprising contacting the gaseous stream with a strong acid.

3. The method of claim 2 wherein the strong acid is phosphoric acid or sulfuric acid.

4. The method of claim 2 wherein x is an integer from 7 to 14 and y is an integer from 7 to 14.

5. The method of claim 4 wherein the weight ratio of the first amine to the second amine is about 4:1.

6. A composition comprising an amine composition comprising a mixture of at least two sterically hindered amines comprising a first amine with the formula:

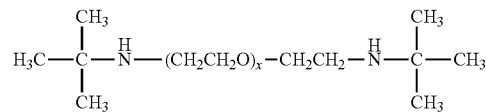

and a second amine with the formula:

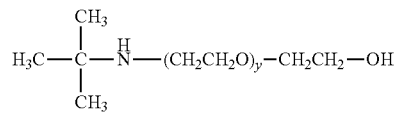

wherein x is an integer from 7 to 14; y is an integer from 3 to 14 and the weight ratio of the first amine to the second amine is about 2.5:1 to about 6:1, and a liquid medium comprising water or an organic solvent or a mixture thereof.

7. The composition of claim 6 further comprising a strong acid.

* * * * *